United States Patent
Ba et al.

(10) Patent No.: US 10,627,380 B2
(45) Date of Patent: Apr. 21, 2020

(54) MULTI-SOURCE DATA ASSIMILATION FOR THREE-DIMENSIONAL ENVIRONMENTAL MONITORING

(71) Applicant: International Business Machines Corporation, Armonk, NY (US)

(72) Inventors: Yu Tao Ba, Beijing (CN); Wen Chen Cheng, Beijing (CN); Chang Rui Ren, Beijing (CN); Ling Yun Wang, Beijing (CN); Wen Jun Yin, Beijing (CN); Gang Zhou, Beijing (CN); Ke Xu Zou, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 236 days.

(21) Appl. No.: 15/427,229

(22) Filed: Feb. 8, 2017

(65) Prior Publication Data

US 2018/0224415 A1    Aug. 9, 2018

(51) Int. Cl.
*G01N 33/00* (2006.01)
*G06F 16/27* (2019.01)
(Continued)

(52) U.S. Cl.
CPC ..... *G01N 33/0034* (2013.01); *G01N 33/0032* (2013.01); *G01S 17/88* (2013.01);
(Continued)

(58) Field of Classification Search
CPC ............ G01N 33/0034; G01N 33/0032; G06F 17/3097; G01S 17/88
See application file for complete search history.

(56) References Cited

U.S. PATENT DOCUMENTS 7,302,313 B2    11/2007  Sharp et al.
2015/0117767 A1*  4/2015  Gong ................... G06K 9/00
                                                  382/160
(Continued)

FOREIGN PATENT DOCUMENTS

CN    106124374 A    11/2016
EP       2687844 A2    1/2014
WO     02063539 A1    8/2002

OTHER PUBLICATIONS

H. Eskes et al., "Data Assimilation and Air Quality Forecasting," Air Pollution Modeling and Its Application XXII, NATO Science for Peace and Security Series C: Environmental Security, May 7, 2013, pp. 189-192.
(Continued)

*Primary Examiner* — Stephanie E Bloss
(74) *Attorney, Agent, or Firm* — Joseph Petrokaitis; Ryan, Mason & Lewis, LLP (57) ABSTRACT

The disclosure involves multi-source data assimilation. According to an embodiment, first data associated with an indication of environmental quality in a first region is obtained, and second data associated with an indication of environmental quality in a second region is obtained. The first data is of a higher quality than the second data according to a predetermined criterion. The second data is calibrated according to a relationship between the first and second data in an overlap of the first and second regions. Third data associated with an indication of environmental quality in a third region is determined based on the first data and the calibrated second data, wherein the third region comprises at least the first and second regions.

20 Claims, 6 Drawing Sheets

(51) Int. Cl.
  *G01S 17/88* (2006.01)
  *G01S 17/95* (2006.01)
(52) U.S. Cl.
  CPC .............. *G01S 17/95* (2013.01); *G06F 16/27* (2019.01); *Y02A 90/19* (2018.01)

(56) References Cited

U.S. PATENT DOCUMENTS

| | | | |
|---|---|---|---|
| 2015/0330817 A1* | 11/2015 | Law | G01D 21/02 702/3 |
| 2016/0116405 A1 | 4/2016 | Bertaux | |
| 2016/0125307 A1* | 5/2016 | Zheng et al. | G06N 3/08 706/12 |
| 2016/0177524 A1* | 6/2016 | Rohrbaugh | E01H 1/00 15/78 |
| 2016/0214715 A1* | 7/2016 | Meffert | B64C 39/024 |
| 2017/0261645 A1* | 9/2017 | Kleeman | G01W 1/10 |
| 2017/0329048 A1* | 11/2017 | Lemos | G01W 1/10 |

OTHER PUBLICATIONS

"Using Light Detection Technology to Examine Air Quality," Maryland Department of the Environment, http://www.mde.maryland.gov/programs/Air/AirQualityMonitoring/Pages/Lidar.aspx, 2017, 1 page.

J. A. Engel-Cox et al., "Qualitative and Quantitative Evaluation of MODIS Satellite Sensor Data for Regional and Urban Scale Air Quality," Atmospheric Environment, May 2004, pp. 2495-2509, vol. 38, No. 16.

* cited by examiner

MULTI-SOURCE DATA ASSIMILATION FOR THREE-DIMENSIONAL ENVIRONMENTAL MONITORING

BACKGROUND

The present invention relates to data processing, and more specifically, to multi-source data assimilation.

In environmental monitoring, multiple sources with varying coverages, accuracies, resolutions, metrics, etc. are monitored. For example, in air quality monitoring, air quality data may be obtained from ground monitoring stations, ground sensors, laser radars, satellites, etc. The ground station data usually has a high accuracy but a small coverage due to the cost, while the ground sensor data has a lower accuracy but a larger coverage than the ground station data. The laser radar data has a three-dimensional (3D) coverage but usually a poor resolution. The satellite aerosol optical depth (AOD) data may have a large coverage but a low accuracy. Therefore, there exists a need for combining or assimilating data sets from different data sources into one data set to better reflect environmental conditions.

SUMMARY

The embodiments disclosed herein include a method, system and computer program product for data assimilation.

According to an embodiment of the present invention, a computer-implemented method is provided. According to the method, first data associated with an indication of environmental quality in a first region are obtained, and second data associated with an indication of environmental quality in a second region are obtained. The first data is of a higher quality than the second data according to a predetermined criterion. The second data is calibrated according to a relationship between the first and second data in an overlap of the first and second regions. Third data associated with an indication of environmental quality in a third region is determined based on the first data and the calibrated second data, wherein the third region comprises at least the first and second regions.

According to another embodiment of the present invention, a system is provided, which comprises a processor and a computer-readable memory unit coupled to the processor. The processor is configured to obtain first data associated with an indication of environmental quality in a first region and obtain second data associated with an indication of environmental quality in a second region. The first data is of a higher quality than the second data according to a predetermined criterion. The second data is calibrated according to a relationship between the first and second data in an overlap of the first and second regions. Third data associated with an indication of environmental quality in a third region is determined based on the first data and the calibrated second data, wherein the third region comprises at least the first and second regions.

According to another embodiment of the present invention, a computer program product is provided, which comprises a computer readable storage medium having program instructions embodied therewith. The program instructions are executable by a processor to cause the processor to obtain first data associated with an indication of environmental quality in a first region and obtain second data associated with an indication of environmental quality in a second region. The first data is of a higher quality than the second data according to a predetermined criterion. The second data is calibrated according to a relationship between the first and second data in an overlap of the first and second regions. Third data associated with an indication of environmental quality in a third region is determined based on the first data and the calibrated second data, wherein the third region comprises at least the first and second regions.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

Figure 1:
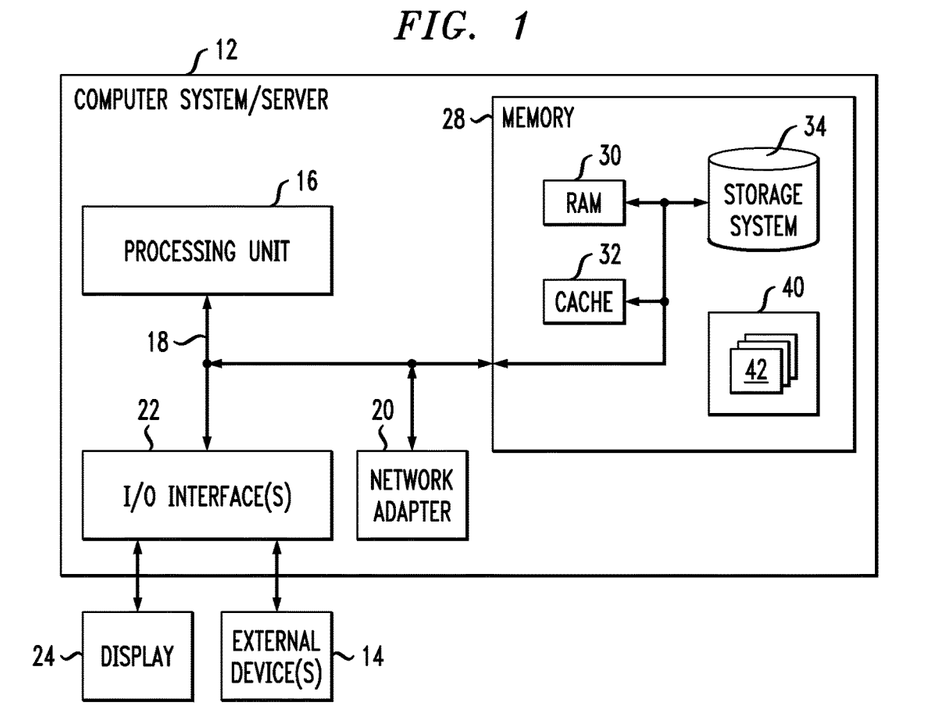
FIG. 1 depicts an exemplary computer system which is applicable to implement the embodiments of the present invention.

Referring now to FIG. 1, in which an exemplary computer system/server 12 which is applicable to implement the embodiments of the present invention is shown. Computer system/server 12 is only illustrative and is not intended to suggest any limitation as to the scope of use or functionality of embodiments of the invention described herein.

As shown in FIG. 1, computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Some embodiments of the present invention may be implemented as the program/utility 40 or the program modules 42 of FIG. 1, which may be at least part of the data assimilation system. Now, with reference to FIGS. 2-5, some embodiments of the present invention will be described below.

Data assimilation methods have been developed, which are applied in many fields of geosciences, especially in atmosphere simulation, weather forecast and hydrology. Most conventional data assimilation methods use numerical models (e.g., WRF-Chem (Weather Research and Forecasting model coupled with Chemistry), GFS (Global Forecast System), etc.) with real-time observation data as their constraints. However, the computational cost of these conventional data assimilation methods usually increases very fast when the size of observation data increases, and the error decreases very slow when the size of observation data is large. In other words, it is hard for conventional data assimilation methods to satisfy both low computational cost and high precision.

Figure 2:
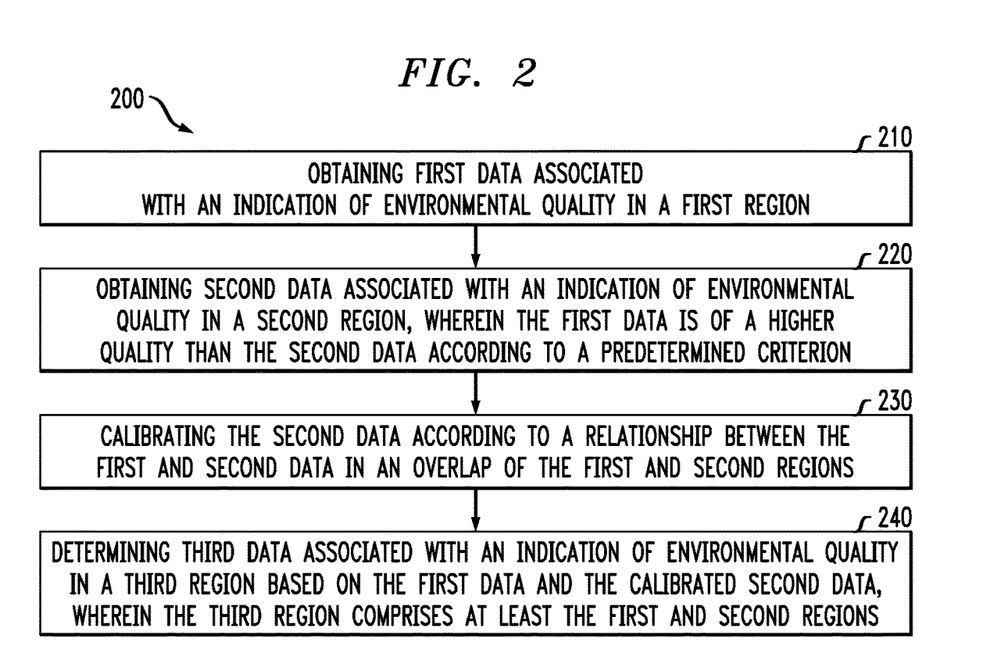
FIG. 2 depicts a flow chart showing an exemplary method for assimilating two data sets according to an embodiment of the present invention.

FIG. 2 shows an exemplary method 200 for assimilating two data sets associated with indications of environmental qualities in first and second regions into one data set, according to an embodiment of the present invention. The resulting data set may be associated with an indication of environmental quality in a predetermined third region (i.e., a target region) comprising at least the first and second regions. After the two data sets are assimilated, more data sets can be further assimilated by iteratively performing method 200 or its variants.

As shown in block 210, first data associated with an indication of environmental quality in a first region is obtained. And as shown in block 220, second data associated with an indication of environmental quality in a second region is obtained. It should be noted that, although FIG. 2 shows block 220 as following block 210, block 220 can alternatively be performed prior to block 210 or concurrently with block 210. The operations in these two blocks can be performed independently and there is no limitation to their sequence.

Here, the term "region" may refer to a two-dimensional (2D) region (e.g., a polygon on the ground) or a three-dimensional (3D) region (e.g., a cube in the atmosphere). Accordingly, the first and second data may indicate environmental quality at points in the 2D region or at points in the 3D region. The first and second regions may have the same dimension or have different dimensions, which is not limited. The environmental quality data in the first and second regions may have the same metric or different metrics, which is also not limited. For example, the first region may be a polygonal area on the ground, and the first data in the first region may be particulate concentration (e.g., concentration of particulate matter (PM) 2.5). The second region may be another polygonal area on the ground, and the second data in the second region may also be particulate concentration. As another example, the first region may be a polygonal area on the ground and the first data in the first region may be particulate concentration. The second region may be a cube in the atmosphere extending upward from the ground, and the second data in the second region may be extinction measured by laser radar, which can also reflect particulate concentration.

For the sake of description, it is assumed that the first data is of a higher quality than the second data according to a predetermined criterion. Accordingly, the first data can be used to calibrate the second data. More detailed descriptions will be described with reference to block 230. The predetermined criterion may include at least one of: coverages of the first and second regions, measurement accuracies of the first and second data, and/or measurement resolutions of the first and second data. For example, the data having a higher accuracy can be defined as the first data and be used to calibrate the second data.

According to an embodiment, the number or density of points in the third region may depend on a predetermined resolution. To facilitate data processing, in one embodiment, grids may be generated in the third region according to the predetermined resolution, such that a higher resolution corresponds to denser grids in the third region, and each grid may represent a point in the third region. Usually, if the first region and the second region have different dimensions, the third region may have the same dimension as the one of the first and second regions having the higher dimension. For example, if the first region is a 2D ground region while the second region is a 3D atmosphere region, the third region will be a 3D atmosphere region comprising at least the first and second regions.

According to an embodiment, the first data may include first measured data obtained by performing a measurement at one or more first observation points in the first region and first interpolated data obtained by performing an interpolation at one or more other points in the first region based on the first measured data. The points to be interpolated in the first region may depend on the predetermined resolution of the third region. Similarly, the second data may include second measured data obtained by performing a measurement at one or more second observation points in the second region and second interpolated data obtained by performing an interpolation at one or more other points in the second region based on the second measured data. The points to be interpolated in the second region may also depend on the predetermined resolution of the third region.

To help understand the embodiments described herein, an example of method 200 will be described in connection with FIGS. 3-4. In this example, the first region and the second region are both 2D regions, but it is to be understood an appreciated that one or more of the regions may be a 3D region.

Figure 3A:
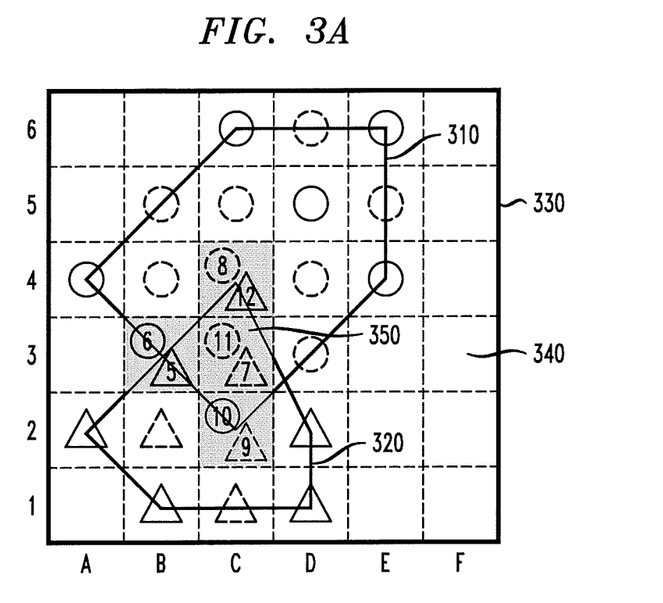
FIGS. 3A and 3B depict an example of assimilating two data sets according to an embodiment of the present invention.

As shown in FIG. 3A, the first region is indicated by polygon 310, the second region is indicated by polygon 320, and the third region is indicated by square 330. Points in the first region 310 are shown as circles and points in the second region 320 are shown as triangles. The third region 330 is shown comprising a 6×6 grid (squares A1-F6), with each square of the grid corresponding to a point in the third region 330. The part in the third region 330 not covered by the first and second regions 310 and 320 is referred to herein as the fourth region 340, which is shown in FIG. 3A as not populated by any circles or triangles.

To obtain the first data in the first region, environmental quality data at one or more first observation points is obtained by performing a measurement. The one or more first observation points may include, for example, one or more points equipped with similar observation instruments (e.g., air quality monitoring stations), so that the first data at the first observation points may be measured in the same way and thus have the same or similar metric and accuracy. In FIG. 3A, the first observation points are shown as solid-line circles.

The first region may be a region covering at least the first observation points. For example, the distribution of the first observation points can determine a convex hull of the first observation points, which may serve as the first region 310. If there are points in the first region 310 that have no measured data, these points may be interpolated using the measured data at the first observation points, such that all points in the first region have environmental quality data. In FIG. 3A, the interpolated points in the first region 310 are shown as dotted-line circles.

The second data in the second region 320 can be obtained in a similar way. Specifically, environmental quality data at one or more second observation points are obtained by performing a measurement. The second observation points may include, for example, one or more points equipped with similar observation instruments other than those for the first observation points (e.g., air quality sensors having lower accuracy than the air quality monitoring stations), so that the second data at the second observation points may be measured in the same way and thus have the same or similar metric and accuracy, although they may be substantially different from those at the first observation points. In FIG. 3A, the second observation points are shown as solid-line triangles.

The first region may be a region covering at least the second observation points. For example, the distribution of the second observation points can determine a convex hull of the second observation points, which may serve as the second region 320. If there are points in the second region 320 that have no measured data, these points may be interpolated using the measured data at the second observation points, such that all points in the second region have environmental quality data. In FIG. 3A, the interpolated points in the second region 320 are shown as dotted-line triangles.

Refer back to FIG. 2. At block 230, the second data in the second region is calibrated according to a relationship between the first and second data in an overlap of the first and second regions.

The calibration at block 230 will be described in more detail below with reference to FIGS. 3-4. As shown in FIG. 3A, there is an overlap region 350 of the first region 310 and the second region 320, which contains four overlap points (or squares): B3, C2, C3 and C4. In this case, there is one first data and one second data at each overlap point. Exemplary data at these points are shown in FIG. 3A. Specifically, the first data at points B3, C2, C3, and C4 are 6, 10, 11, 8, respectively, and the second data at points B3, C2, C3, and C4 are 5, 9, 7, 12, respectively. Assuming that the first data are of a higher quality than the second data, the second data may be calibrated according to the relationship between the first and second data in the overlap 350. In the case where the first data and second data have different metrics or units, the calibration may also include unifying the units, usually by converting the unit of the second data to the unit of the first data.

Figure 3B:
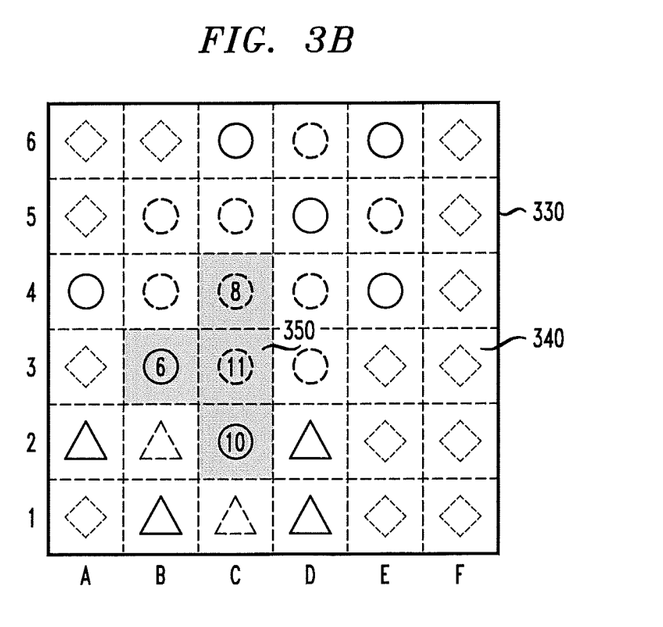

According to an embodiment, the second data at a given overlap point in the overlap 350 may be replaced with the first data at the given overlap point, as shown in FIG. 3B. In other words, the calibrated second data at a given overlap point in the overlap 350 can be the first data at the given overlap point.

According to an embodiment, a fitted curve may be constructed to indicate the relationship between the first and second data at each overlap point in the overlap 350. As an example, FIG. 4 shows an exemplary fitted curve 410 indicating the relationship between the first data and second data at overlap points B3, C2, C3 and C4. In the plot of FIG. 4, the horizontal axis x represents the second data and the vertical axis y represents the first data, and the constructed curve 410 corresponds to a linear function $y=1.5x-1$. It is to be understood and appreciated that the linear fitting as shown in FIG. 4 is merely an example, and the fitted curve may be embodied in a variety of forms, such as a polynomial function, a trigonometric function, etc.

The fitted curve 410 can be used to calibrate the second data in the second region 320 at points other than the overlap points of the overlap 350. Specifically, the second data at points A2, B1, B2, C1, D1 and D2 can each be used as the input x of the linear function $y=1.5x-1$ and the calibrated second data can be the output y. For example, if the second data at point A2 is 12, then the calibrated second data at point A2 is calculated as 17.

Refer back again to FIG. 2. At block 240, third data associated with an indication of environmental quality in the third region is determined based on the first data and the calibrated second data. In one embodiment, the third region may be a predetermined target region that needs a complete set of environmental quality data at each point therein. As noted above, the third region may comprise at least the first and second regions. For example, as shown in FIGS. 3A and 3B, the third region 330 is a square larger than the combination of the first and the second regions.

The operation at block 240 will be described in more detail below with reference to FIGS. 3-4. According to an embodiment, for the points in the first and second regions, the first data may be used as the third data in the first region, and the calibrated second data may be used as the third data in the second region, as shown in FIG. 3B.

According to an embodiment, for the points in the third region other than the first and second regions (i.e., the points in the fourth region 340 in FIGS. 3A-3B), the third data (as shown by the diamonds in FIG. 3B) may be determined by performing an extrapolation based at least in part on the first data and the calibrated second data. In one embodiment, the third data in the region 340 may be determined based on all of the first data and calibrated second data. In another embodiment, the third data in the region 340 may be determined based on part of the first data and calibrated second data, such as the first data and the calibrated second data at the observations points (e.g., the solid-line circles and solid-line triangles in FIG. 3B).

According to an embodiment, weights for the extrapolation may be determined based at least on one or more reliabilities of the first data and one or more reliabilities of the calibrated second data. Moreover, the weights may be determined further based on the distance between the point to be extrapolated and the point to be weighted. The reliability for each point in the first region may be the same or different. Also, the reliability for each point in the second region may be the same or different. Some embodiments for determining the reliabilities and weights will be described below with reference to some exemplary equations.

According to an embodiment, the one or more reliabilities of the calibrated second data are related to the consistency of deviation between the first and second data in the overlap. Specifically, with the assumption that the first data is of a higher quality (e.g., higher accuracy) than the second data, the first data is usually considered as more reliable than the second data. From the relationship between the first and second data in the overlap, the consistency of deviation between the first and second data can be obtained, and in turn the reliability of the calibrated second data can be determined. For example, in the plot of FIG. 4, should the fitted curve 410 exactly fit the four dots corresponding to points B3, C4, C3 and C2, the second data would be considered to have a high consistency of deviation, and the reliability of the calibrated second data would be rather high. Usually, the more the dots in FIG. 4 that deviate from the fitted curve 410, the lower the consistency of deviation between the first and second data and thus the reliability of the second calibrated data is lower.

For example, the consistency of deviation between the first and second data in the overlap may be calculated as follows:

$$C = \frac{1}{n}\sum_{i=1}^{n}\left(\frac{x_i - \bar{x}}{\sigma_x}\right)\left(\frac{y_i - \bar{y}}{\sigma_y}\right) \quad \text{(Eq. 1)}$$

Here, C is the consistency of deviation between the first and second data in the overlap, n is the number of points in the overlap, $x_i$ is the second data, $y_i$ is the first data, $\bar{x}$ and $\sigma_x$ are the average and standard deviation of $x_i$, respectively, and $\bar{y}$ and $\sigma_y$ are the average and standard deviation of $y_i$, respectively.

Figure 4:
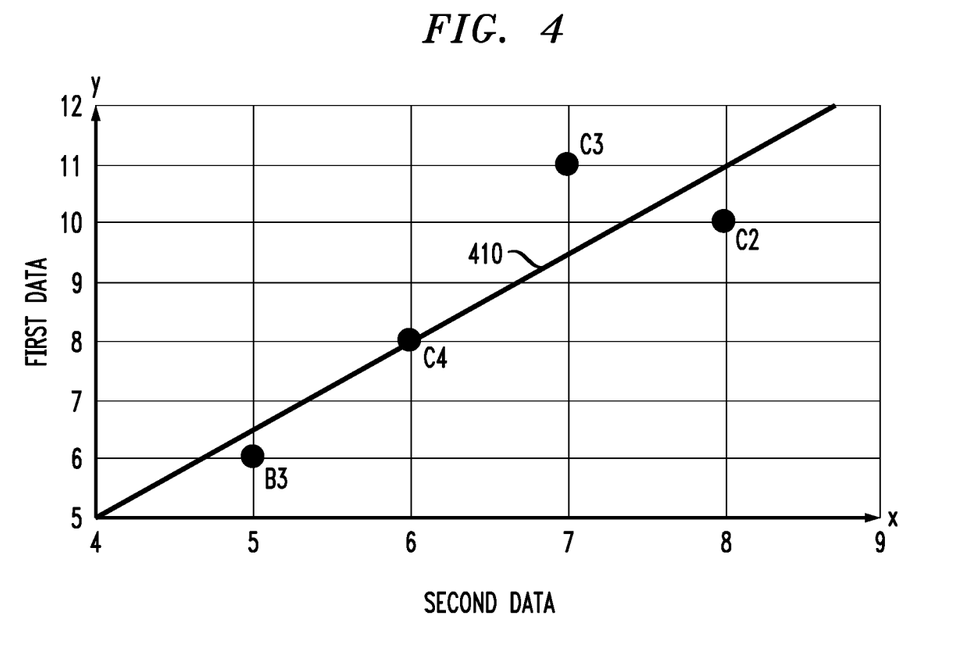
FIG. 4 depicts a plot indicating an exemplary relationship between two data sets in the overlapped region according to an embodiment of the present invention.

Take FIG. 4 as an example. As shown in FIG. 4, n=4, $x_1$=5, $x_2$=6, $x_3$=7, $x_4$=8, $y_1$=6, $y_2$=8, $y_3$=11, $y_4$=10. So, the consistency C is calculated as 0.87 according to (Eq. 1).

Then the reliability R2 of the calibrated second data can be calculated as $$R2 = C \times \overline{R1} \quad \text{(Eq. 2)}$$

where $\overline{R1}$ is the average reliability of the first data in the overlap.

For example, in air quality monitoring, assuming that the first data is obtained from ground monitoring stations and has the highest reliability of 1, then the calibrated second data (such as the air quality data from ground sensors) may have a reliability of 0.87. It should be noted that, although in this example, all the first data have the reliability of 1, in other examples, the reliabilities of the first data at different points in the overlap may be different.

Then, extrapolation may be performed for the points in the fourth region 340 with weights calculated based on the reliabilities of the first and calibrated second data. For example, for point k (e.g., the point of square E3 in FIGS. 3A-3B) in the fourth region 340, the extrapolated data can be calculated as follows:

$$D4_k = \Sigma_i W1_{ki} \times D1_i + \Sigma_j W2_{kj} \times D2_j \quad \text{(Eq. 3)}$$

Here, $D1_i$ is the first data at point i in the first region 310, $D2_j$ is the calibrated second data at point j in the second region 320, $D4_k$ is the extrapolated data at point k in the fourth region 340, $W1_{ki}$ is the weight for point i in the first region, and $W2_{kj}$ is the weight for point j in the second region. $W1_{ki}$ and $W2_{kj}$ can be calculated as follows:

$$W1_{ki} = P \times 1/\exp(dis_{ki}/R1_i) \quad \text{(Eq. 4)}$$

$$W2_{kj} = P \times 1/\exp(dis_{kj}/R2_j) \quad \text{(Eq. 5)}$$

Here, $dis_{ki}$ is the distance between point i and point k, $dis_{kj}$ is the distance between point j and point k, $R1_i$ is the reliability of the first data at point i, $R2_j$ is the reliability of the calibrated second data at point j, and P is the scale factor to satisfy $\Sigma_i W1_{ki} + \Sigma_j W2_{kj} = 1$.

According to an embodiment, all points in the first region 310, including observation points and interpolated points, may be used as the point i in (Eq. 3) for extrapolation, and all points in the second region 320, including observation points and interpolated points, may be used as the point j in (Eq. 3) for extrapolation. According to another embodiment, only the observation points in the first region 310 (shown as the solid-line circles) may be used as the point i in (Eq. 3), and only the observation points in the second region 320 (shown as the solid-line triangles) may be used as the point j in (Eq. 3).

It should be noted that, the above equations for calculating the consistency, reliability and extrapolated data are merely examples and not limitations. For example, the consistency C may be calculated using other methods than (Eq. 1), as long as it can reflect the consistency of deviation between the first and second data in the overlap in accordance with the embodiments described herein. The reliability may be calculated using other methods than (Eq. 2), as long as it is related to the consistency C in accordance with the embodiments described herein. The calculation of weights is also not limited to (Eq. 4) and (Eq. 5), but may be any method that can reflect the effect of data reliability on the weights in accordance with the embodiments described herein. Moreover, the calculation of the extrapolated data D4 in the fourth region is not limited to (Eq. 3), but may be other extrapolation methods taking the calculated weights into account in accordance with the embodiments described herein.

Further, although in the above embodiment the first data may directly serve as the third data in the first region and the calibrated second data may directly serve as the third data in the second region, there may be other variants. For example, for each point in the first and second regions, the third data may be a weighted average of the first and second data, e.g., calculated in a way similar to (Eq. 3).

With block 240 performed, the third region 330 is filled in with data, and thus a complete data set reflecting the whole environmental conditions in the third region 330 is obtained, which has a relatively low computational cost, a high accuracy, and a satisfactory resolution and coverage.

As previously mentioned, after the two data sets are combined into one data set, more data sets can be assimilated by iteratively performing method 200 or its variants. For further assimilation, the third region may be used as the first or second regions for the next iteration. This may be determined based on the characteristics of the data in the third region and the new data set to be further assimilated, such as the coverage, accuracy, resolution, etc.

To perform the next iteration, one or more reliabilities of the third data in the third region may be required. According to an embodiment, the reliabilities of the third data in the first and second regions can be the reliabilities of the corresponding first and second data at the same point. For the third data in the fourth region, which are obtained by extrapolation, the reliabilities may be calculated based on the reliabilities of the first and second data. As an example, for point k (e.g., the point of square E3 in FIGS. 3A-3B) in the fourth region 340, the reliability of the third data can be calculated as follows:

$$R4_k = \Sigma_i U1_{ki} \times R1_i + \Sigma_j U2_{kj} \times R2_j \quad \text{(Eq. 6)}$$

Here, $R1_i$ is the reliability of the first data at point i in the first region 310, $R2_j$ is the reliability of the calibrated second data at point j in the second region 320, $R4_k$ is the reliability of the extrapolated data at point k in the fourth region 340, $U1_{ki}$ is the weight for point i in the first region, and $U2_{kj}$ is the weight for point j in the second region. $U1_{ki}$ and $U2_{kj}$ can be calculated as follows:

$$U1_{ki} = Q \times 1/\exp(dis_{ki}) \quad \text{(Eq. 7)}$$

$$U2_{kj} = Q \times 1/\exp(dis_{kj}) \quad \text{(Eq. 8)}$$

Here, $dis_{ki}$ is the distance between point i and point k, $dis_{kj}$ is the distance between point j and point k, and Q is the scale factor to satisfy $\Sigma_i U1_{ki} + \Sigma_j U2_{kj} = 1$.

It should be noted that, the above equations for calculating the reliability for the extrapolated data in the fourth region 340 are merely an example and not limitation. The reliability may be calculated using other methods than (Eq. 6) in accordance with the embodiments described herein.

According to an embodiment, in the next iteration of method 200, the squares of the grid may be re-generated according to the coverage and dimension of the next target region to be filled in.

According to an embodiment, in the next iteration of method 200, if the next target region is equal to or smaller than the third region 330, all the points in the target region already have data and there is no need to fill in the target region. However, in such a case, the new data set to be assimilated may be used to further modify the third data by performing a weighted average of the new data set and the third data. The weights may be determined based at least on the reliabilities of the data.

Now, a specific example of air quality data assimilation using the method according to the present invention will be described with reference to FIGS. 5A-5D.

In the field of air quality monitoring, it is usually required to obtain the air quality data at any point in a particular 3D space, i.e., obtain a full-coverage map of air quality data with enough resolution and satisfactory accuracy. However, data assimilation in this field is difficult especially due to the large variance of data quality, coverage and resolution across different data sets.

In this example, the air quality data may come from several sources including, but not limited to, ground stations, ground sensors, laser radars and satellites. The data from ground stations and ground sensors are PM 2.5 concentration, the data from laser radars are extinctions, and the data from satellites are aerosol optical depths (AODs). In this example, at the first stage, the ground station data and the ground sensor data may be combined to obtain the data at the ground level, then at the second stage, the laser radar data may be combined with the ground level data to obtain the data in the 3D space, and at the third stage, the satellite data may be combined with the data in the 3D space obtained at the second stage. The final air quality map will reflect the air quality distribution in the 3D space extending upward from a particular ground area, e.g., a city.

Figure 5A:
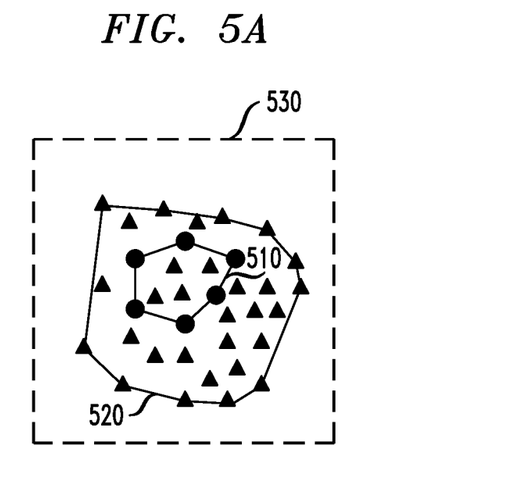
FIGS. 5A-5D depict an example of multi-source air quality data assimilation according to an embodiment of the present invention.

At the first stage, as shown in FIG. 5A, the solid circles represent the ground stations, and the corresponding first region 510 is a region covering at least the ground stations. For example, the first region 510 may be a convex hull of the ground stations at the ground level. The solid triangles represent the ground sensors, and the corresponding second region 520 is a region covering at least the ground sensors. For example, the second region 520 may be a convex hull of the ground sensors at the ground level. The target region at the first stage is a square indicated by 530, which may represent the ground level of a city whose air quality distribution is required. It can be seen that the ground stations usually have lower coverage than the ground sensors, but they usually have a higher accuracy. Although not shown in FIG. 5A, 2D grids may be generated in the target region 530 with a resolution of, e.g., 1×1 km. If necessary, the grids in the first region 510 and the second region 520 can be filled in by interpolation based on the observations of the ground stations and the ground sensors, respectively.

Figure 5B:
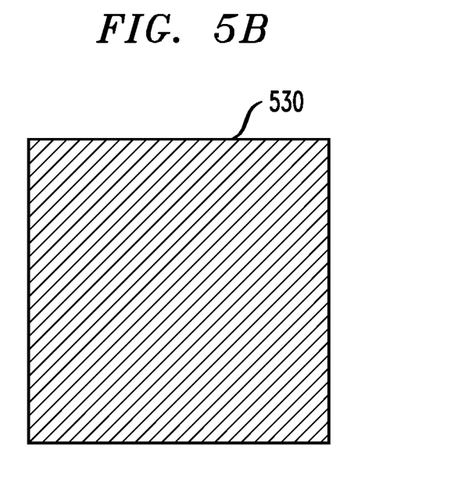

In this example, the overlap of the first and second regions is the first region 510. After calibrating the ground sensor data and filling in the target region 530 according to method 200, a complete set of ground level data in the target region 530 is obtained, as shown in FIG. 5B, in which the spaced-line shading means the target region 530 has been filled in with data. Moreover, the reliability of each point in the target region 530 can be determined according to the embodiments described above with reference to FIGS. 2-4. Specifically, the reliability of points in the region 510 may be set as 1, the reliability of points in the second region 520 other than the overlap 510 may be determined according to the consistency of deviation between the two data sets in the overlap 510, e.g., according to (Eq. 1) and (Eq. 2), and the reliabilities of points in the part of region 530 outside the second region 520 may be determined according to, e.g., (Eq. 6). Since both the ground station data and the ground sensor data are PM 2.5 concentration, unit conversion may not be necessary.

Figure 5C:
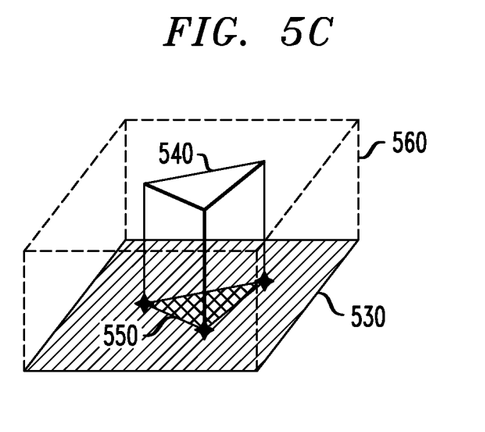

Then, at the second stage, the laser radar data may be combined with the ground level data in FIG. 5B to obtain the air quality data in the 3D space upward from the region 530. As shown in FIG. 5C, the solid stars represent the laser radars, which can measure air quality data in the space upward from where it is located on the ground. For example, it may measure the air quality data from the ground to 5 km above the ground with a vertical resolution of 200 meters. There are three laser radars in this example, and the region covering the measured points of the laser radars (e.g., a convex hull of the measured points of the laser radars) is shown as the 3D region 540, which is a triangular prism. The target region 560 at the second stage is also a 3D region upward from the ground region 530 and to be filled in with air quality data. Although not shown in FIG. 5C, 3D grids may be generated in the target region 560 with a resolution of, e.g., 1 km×1 km×200 m. If necessary, the grids in the triangular prism 540 can be filled in by interpolation based on the observations of the laser radars.

Figure 5D:
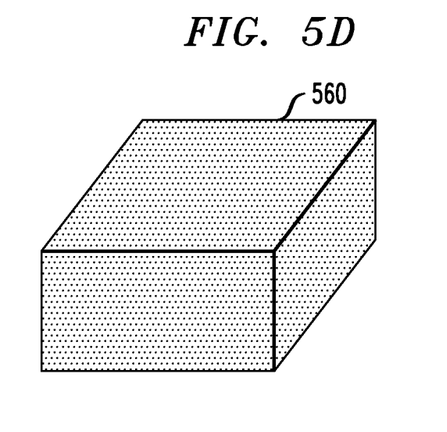

The overlap of the region 530 and the region 540 is the triangle 550 on the ground, as shown by the cross-line shading in FIG. 5C. Assuming that the ground level data has a higher accuracy than the laser radar data, the ground level data obtained in the first stage and the laser radar data may be used as the first and second data respectively at the second stage. Thus, the laser radar data may be calibrated with respect to the ground level data according to method 200, and then the whole 3D region 560 can be filled in by extrapolation. As such, a complete data set for the 3D target region 560 is obtained, as shown in FIG. 5D, in which the dot shading means the target region 560 has been filled in with data. Moreover, the reliability of each point in the target region 560 can be determined according to the embodiment as described above with reference to FIGS. 2-4. Specifically, the reliabilities of points in the region 530 may have been determined at the first stage, the reliability of points in the triangular prism 540 other than the overlap 550 may be determined according to the consistency of deviation between the two data sets in the overlap 550, e.g., according to (Eq. 1) and (Eq. 2), and the reliabilities of points in the part of target region 560 other than the regions 530 and 540 may be determined according to, e.g., (Eq. 6). It should be noted that, usually the laser radar data have a different metric or unit (such as extinction) from the ground level data, so the unit conversion may be required for the laser radar data during the calibration.

At the third stage, the satellite data may be further combined with the data set in the whole 3D region 560, which is not shown in FIG. 5. If the target region is to be further expanded at the third stage, then the assimilation may be made in a way similar to the first or second stage. On the other hand, if the target region is not to be expanded any more at the third stage, the satellite data may be interpolated if necessary, calibrated, and then used to further modify the data set in the region 560 determined at the second stage. The modification may be performed using a weighted average of the data set in the 3D region 560 determined at the second stage and the satellite data, and the weights may be determined based at least on the reliabilities of the two data sets. The reliabilities of points in the region 560 may have been determined at the second stage, and the reliabilities of the satellite data may be determined according to the consistency of deviation between the two data sets in the overlap according to (Eq. 1) and (Eq. 2). In the case that the satellite data is a 2D plane distribution instead of a 3D space distribution, it can be expanded vertically with reference to the vertical distribution of the 3D data set obtained at the second stage to facilitate the data processing. Alternatively, the 3D data set obtained at second stage may be averaged vertically to obtain a 2D data set and then combined with the 2D satellite data set. It should be noted that, usually the satellite data have a different metric or unit (such as AOD) from the existing data in the region 560, so unit conversion may be required for the satellite data during the calibration.

With the four data sets from ground stations, ground sensors, laser radars and satellites assimilated, a 3D map indicating the air quality distribution in the target 3D space extending upward from the city can be obtained.

It should be noted that, the above data sources for air quality monitoring are only examples and should not be considered limiting. Other data sources can be assimilated according to embodiments of the present invention, and the method can be applied in other field that needs data assimilation. The data sources to be assimilated can be selected according to, e.g., the requirement for the data. Moreover, the sequence of assimilation for the data sources may be varied considering e.g., the characteristics of the data sources, such as the coverage, accuracy, resolution and so on.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
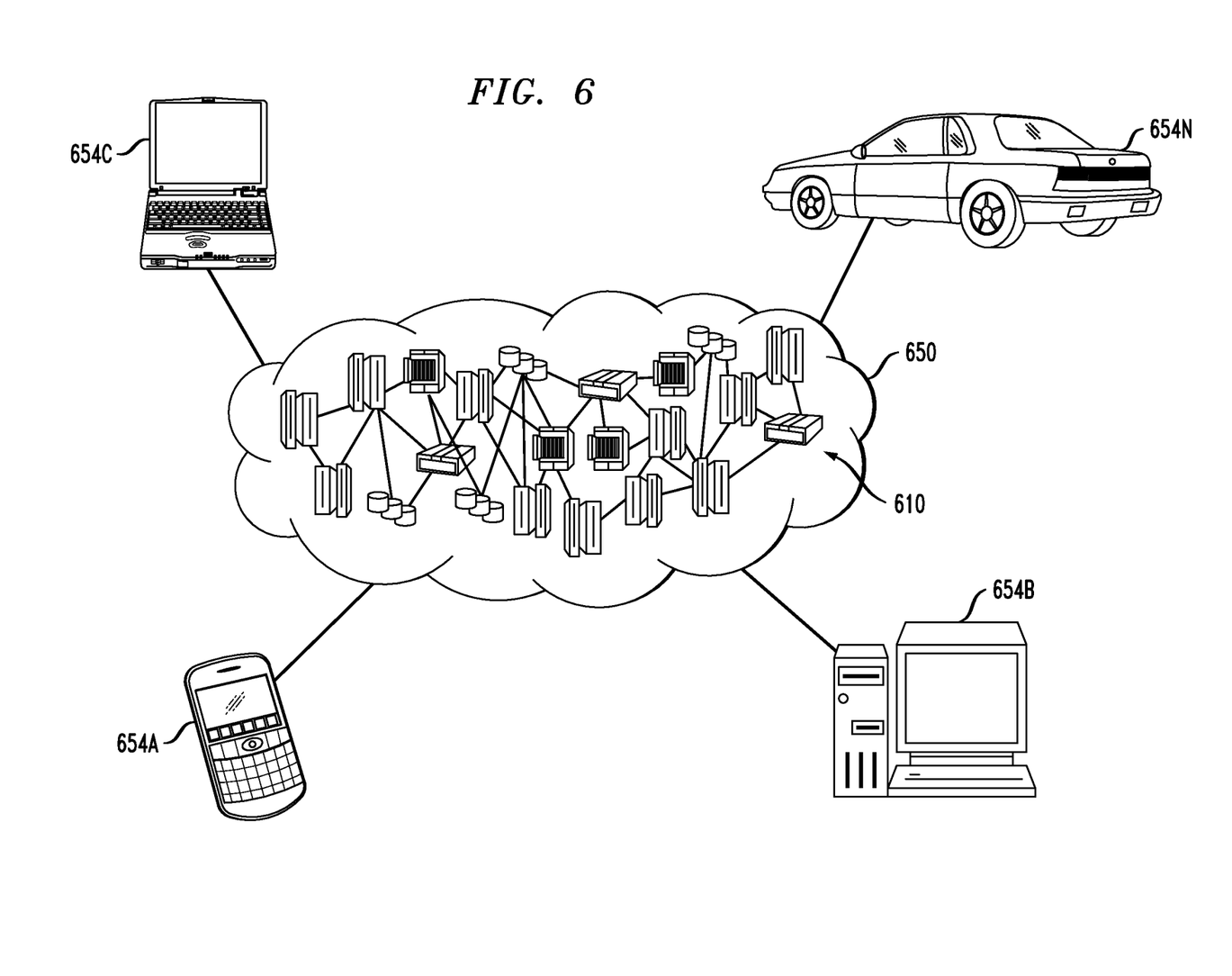
FIG. 6 depicts a cloud computing environment according to an embodiment.

Referring now to FIG. 6, illustrative cloud computing environment 650 is depicted. As shown, cloud computing environment 650 comprises one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
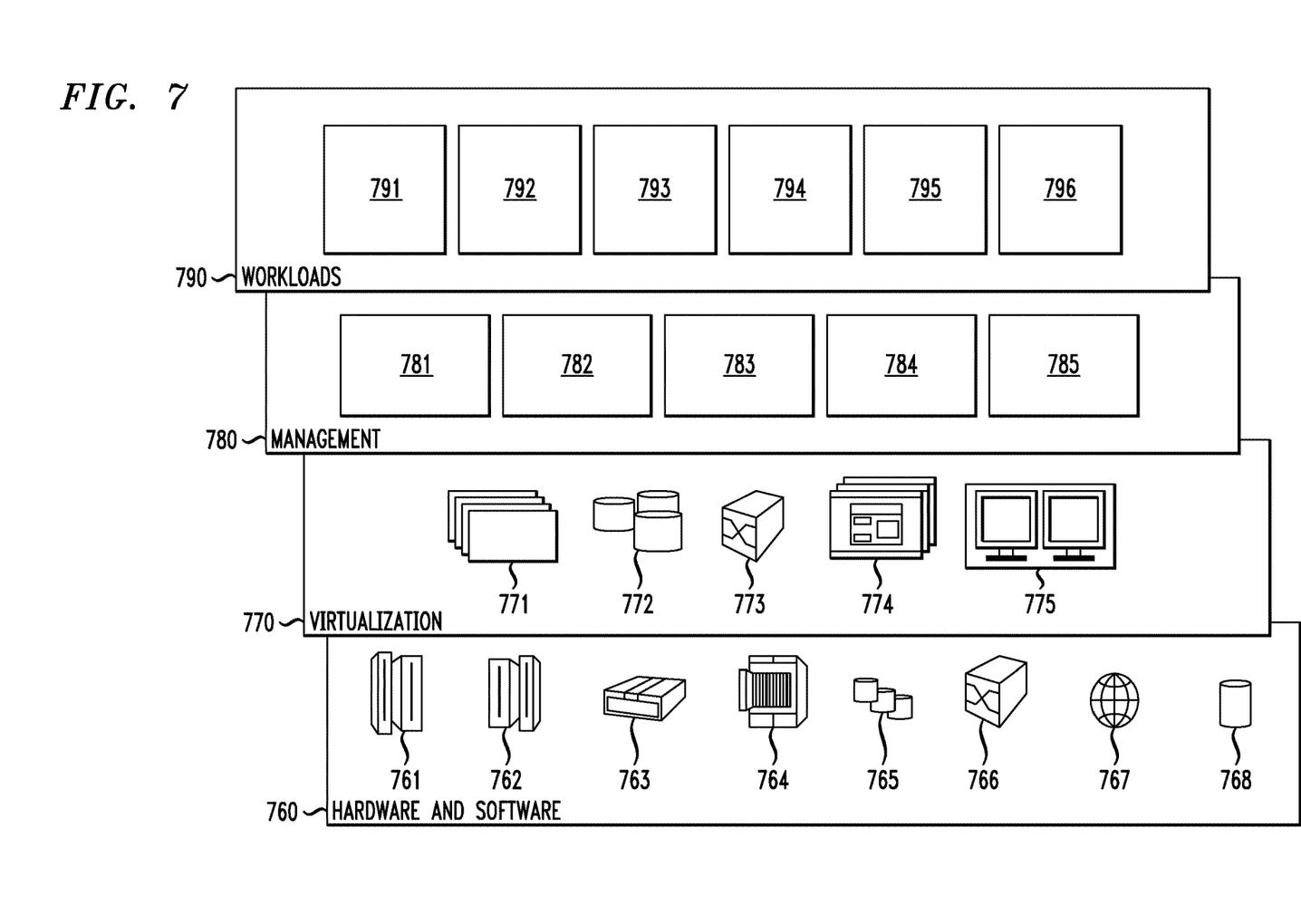
FIG. 7 depicts abstraction model layers according to an embodiment.

Referring now to FIG. 7, a set of functional abstraction layers provided by cloud computing environment 650 (FIG. 6) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; data capturing 793; data analytics processing 794; transaction processing 795; and data assimilation processing 796, which may perform one or more of the functions described above.

The present invention may be a system, a method, and/or a computer program product. The computer program product may include a computer readable storage medium (or media) having computer readable program instructions thereon for causing a processor to carry out aspects of the present invention.

According to an embodiment of the present invention, there is provided a system comprising a processor and a computer-readable memory unit coupled to the processor. The processor is configured to: obtain first data associated with an indication of environmental quality in a first region; obtain second data associated with an indication of environmental quality in a second region, wherein the first data is of a higher quality than the second data according to a predetermined criterion; calibrate the second data in the second region according to a relationship between the first and second data in an overlap of the first and second regions; and determine third data associated with an indication of environmental quality in a third region based on the first data and the calibrated second data, wherein the third region comprises at least the first and second regions.

According to an embodiment of the system, the first data comprises first measured data obtained by performing a measurement at one or more first observation points in the first region, and first interpolated data obtained by performing an interpolation at one or more other points in the first region based on the first measured data. The second data comprises second measured data obtained by performing a measurement at one or more second observation points in the second region, and second interpolated data obtained by performing an interpolation at one or more other points in the second region based on the second measured data.

According to an embodiment of the system, in calibrating the second data, the processor is further configured to: construct a fitted curve that indicates the relationship between the first and second data in the overlap; in the overlap, use the first data as the calibrated second data; and in the second region other than the overlap, calibrate the second data using the fitted curve.

According to an embodiment of the system, in determining the third data, the processor is further configured to: use the first data as the third data in the first region; use the calibrated second data as the third data in the second region; and perform an extrapolation to determine the third data in the third region other than the first and second regions based on at least part of the first data and the calibrated second data.

According to an embodiment of the system, in performing the extrapolation, the processor is further configured to determine weights for the extrapolation based at least in part on one or more reliabilities of the first data and one or more reliabilities of the calibrated second data.

According to an embodiment of the system, the one or more reliabilities of the calibrated second data are related to consistency of deviation between the first and second data in the overlap.

According to an embodiment of the system, the processor is further configured to determine one or more reliabilities of the third data for use in a next iteration of the actions performed by the processor, wherein the third region is used as one of the first or second regions in the next iteration.

According to another embodiment of the present invention, there is provided a computer program product comprising a computer readable storage medium having program instructions embodied therewith. The program instructions may be executable by a processor to cause the processor to: obtain first data associated with an indication of environmental quality in a first region; obtain second data associated with an indication of environmental quality in a second region, wherein the first data is of a higher quality than the second data according to a predetermined criterion; calibrate the second data in the second region according to a relationship between the first and second data in an overlap of the first and second regions; and determine third data associated with an indication of environmental quality in a third region based on the first data and the calibrated second data, wherein the third region comprises at least the first and second regions.

According to an embodiment of the computer program product, the first data comprises first measured data obtained by performing a measurement at one or more first observation points in the first region, and first interpolated data obtained by performing an interpolation at one or more other points in the first region based on the first measured data. The second data comprises second measured data obtained by performing a measurement at one or more second observation points in the second region, and second interpolated data obtained by performing an interpolation at one or more other points in the second region based on the second measured data.

According to an embodiment of the computer program product, the calibration of the second data further comprises program instructions executable by the processor to: construct a fitted curve that indicates the relationship between the first and second data in the overlap; in the overlap, use the first data as the calibrated second data; and in the second region other than the overlap, calibrate the second data using the fitted curve.

According to an embodiment of the computer program product, the determination of the third data further comprises program instructions executable by the processor to: use the first data as the third data in the first region; use the calibrated second data as the third data in the second region; and perform an extrapolation to determine the third data in the third region other than the first and second regions based at least in part on the first data and the calibrated second data.

According to an embodiment of the computer program product, the performance of the extrapolation further comprise program instructions executable by the processor to determine weights for the extrapolation based at least on one or more reliabilities of the first and one or more reliabilities of the calibrated second data.

According to an embodiment of the computer program product, the one or more reliabilities of the calibrated second data are related to consistency of deviation between the first and second data in the overlap.

According to an embodiment of the computer program product, the program instructions executable by a processor further cause the processor to determine one or more reliabilities of the third data in the third region for use in a next iteration of the actions performed by the processor, wherein the third region is used as one of the first or second regions in the next iteration.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
obtaining first data associated with an indication of a select environmental quality in a first region;
obtaining second data associated with an indication of the select environmental quality in a second region, wherein the first data is of a higher quality than the second data according to a predetermined criterion;
calibrating the second data according to a relationship between the first and second data in an overlap of the first and second regions; and
determining third data associated with an indication of the select environmental quality in a third region based on the first data and the calibrated second data, wherein the third region comprises at least the first and second regions;

wherein the first data comprises first measured data obtained by performing a measurement of particulate matter concentration with a first given type environmental quality sensor at one or more first observation points in the first region;

wherein the second data comprises second measured data obtained by performing a measurement of particulate matter concentration with a second given type environmental quality sensor at one or more second observation points in the second region, the second given type environmental quality sensor being different from the first given type environmental quality sensor; and wherein the steps of obtaining first data, obtaining second data, and calibrating the first data are implemented by one or more processing devices each comprising a processor coupled to a memory, and wherein the processor and the memory are configured to execute program instructions associated with each or the steps.

2. The method of claim 1, wherein:

the first data further comprises first interpolated data obtained by performing an interpolation at one or more other first observation points in the first region based on the first measured data; and the second data further comprises second interpolated data obtained by performing an interpolation at one or more other second observation points in the second region based on the second measured data.

3. The method of claim 1, wherein calibrating the second data comprises:

constructing a fitted curve that indicates the relationship between the first and second data in the overlap;

in the overlap, using the first data as the calibrated second data; and in the second region other than the overlap, calibrating the second data using the fitted curve.

4. The method of claim 1, wherein determining the third data comprises:

using the first data as the third data in the first region;

using the calibrated second data as the third data in the second region; and performing an extrapolation to determine the third data in the third region other than the first and second regions based on at least part of the first data and the calibrated second data.

5. The method of claim 4, wherein performing the extrapolation further comprises determining weights for the extrapolation based at least in part on one or more reliabilities of the first data and one or more reliabilities the calibrated second data.

6. The method of claim 5, wherein the one or more reliabilities of the calibrated second data are related to consistency of deviation between the first and second data in the overlap.

7. The method of claim 5, further comprising determining one or more reliabilities of the third data for use in a next iteration of the method, wherein the third region is used as one of the first or second regions in the next iteration.

8. The method of claim 1, wherein the first measured data and the second measured data have different metrics and wherein calibrating the second data includes unifying the metrics by converting the metric of one of the first measured data and the second measured data to the metric of the other of the first measured data and the second measured data.

9. The method of claim 8, wherein the first given type environmental quality sensor includes a ground monitoring station and the second given type environmental quality sensor includes one of a laser and a satellite.

10. A system, comprising:

a processor; and a computer-readable memory unit coupled to the processor, wherein the processor and the memory unit are configured to execute program instructions including:

obtain first data associated with an indication of a select environmental quality in a first region;

obtain second data associated with an indication of the select environmental quality in a second region, wherein the first data is of a higher quality than the second data according to a predetermined criterion;

calibrate the second data according to a relationship between the first and second data in an overlap of the first and second regions; and determine third data associated with an indication of the select environmental quality in a third region based on the first data and the calibrated second data, wherein the third region comprises at least the first and second regions;

wherein the first data comprises first measured data obtained by performing a measurement of particulate matter concentration with a first given type environmental quality sensor at one or more first observation points in the first geographical region; and wherein the second data comprises second measured data obtained by performing a measurement of particulate matter concentration with a second given type environmental quality sensor at one or more second observation points in the second geographical region, the second given type environmental quality sensor being different from the first given type environmental quality sensor.

11. The system of claim 10, wherein:

the first data further comprises first interpolated data obtained by performing an interpolation at one or more other first observation points in the first region based on the first measured data; and the second data further comprises second interpolated data obtained by performing an interpolation at one or more other second observation points in the second region based on the second measured data.

12. The system of claim 10, wherein, in calibrating the second data, the processor is further configured to:

construct a fitted curve that indicates the relationship between the first and second data in the overlap;

in the overlap, use the first data as the calibrated second data; and in the second region other than the overlap, calibrate the second data using the fitted curve.

13. The system of claim 10, wherein, in determining the third data, the processor is further configured to:

use the first data as the third data in the first region;

use the calibrated second data as the third data in the second region; and perform an extrapolation to determine the third data in the third region other than the first and second regions based on at least part of the first data and the calibrated second data, including determining weights for the extrapolation based at least in part on one or more reliabilities of the first data and one or more reliabilities of the calibrated second data.

14. The system of claim 13, including at least one of the following:

wherein the one or more reliabilities of the calibrated second data are related to consistency of deviation between the first and second data in the overlap; or wherein the processor is further configured to determine one or more reliabilities of the third data for use in a next iteration of the actions performed by the processor, wherein the third region is used as one of the first or second regions in the next iteration.

15. The system of claim 10, wherein the first measured data and the second measured data have different metrics and wherein calibrating the second data includes unifying the metrics by converting the metric of one of the first measured data and the second measured data to the metric of the other of the first measured data and the second measured data.

16. A computer program product, comprising a non-transitory computer readable storage medium having program instructions embodied therewith, the program instructions executable by a processor to cause the processor to:
   obtain first data associated with an indication of a select environmental quality in a first region;
   obtain second data associated with an indication of the select environmental quality in a second region, wherein the first data is of a higher quality than the second data according to a predetermined criterion;
   calibrate the second data according to a relationship between the first and second data in an overlap of the first and second regions; and
   determine third data associated with an indication of the select environmental quality in a third region based on the first data and the calibrated second data, wherein the third region comprises at least the first and second regions;
   wherein the first data comprises first measured data obtained by performing a measurement of particulate matter concentration with a first given type environmental quality sensor at one or more first observation points in the first geographical region; and
   wherein the second data comprises second measured data obtained by performing a measurement of particulate matter concentration with a second given type environmental quality sensor at one or more second observation points in the second geographical region, the second given type environmental quality sensor being different from the first given type environmental quality sensor.

17. The computer program product of claim 16, wherein:
   the first data further comprises first interpolated data obtained by performing an interpolation at one or more other first observation points in the first region based on the first measured data; and
   the second data further comprises second interpolated data obtained by performing an interpolation at one or more other second observation points in the second region based on the second measured data.

18. The computer program product of claim 16, wherein the calibration of the second data further comprises program instructions executable by the processor to:
   construct a fitted curve that indicates the relationship between the first and second data in the overlap;
   in the overlap, use the first data as the calibrated second data; and
   in the second region other than the overlap, calibrate the second data using the fitted curve.

19. The computer program product of claim 16, wherein the determination of the third data further comprises program instructions executable by the processor to:
   use the first data as the third data in the first region;
   use the calibrated second data as the third data in the second region; and
   perform an extrapolation to determine the third data in the third region other than the first and second regions based on at least part of the first data and the calibrated second data, including determining weights for the extrapolation based at least in part on one or more reliabilities of the first data and one or more reliabilities of the calibrated second data, and wherein the one or more reliabilities of the calibrated second data are related to consistency of deviation between the first and second data in the overlap.

20. The computer program product of claim 19, further comprising program instructions executable by the processor to determine one or more reliabilities of the third data for use in a next iteration of the actions performed by the processor, wherein the third region is used as one of the first or second regions in the next iteration.

* * * * *